United States Patent [19]

Elderbaum

[11] 4,117,120

[45] Sep. 26, 1978

[54] MEDICATION FOR HERPES SIMPLEX AND CANKER SORES

[76] Inventor: Gilbert J. Elderbaum, 380 Main St., Wakefield, Mass. 01880

[21] Appl. No.: 767,887

[22] Filed: Feb. 11, 1977

[51] Int. Cl.² .............................................. A61K 35/78
[52] U.S. Cl. .................................................... 424/195
[58] Field of Search ......................................... 424/195

[56] References Cited

U.S. PATENT DOCUMENTS 1,513,298   10/1924   Turrentine ........................... 424/195

OTHER PUBLICATIONS

Husa's Pharm. Dispensing, 5th Ed. (1959), Mack Publishing Co., Easton, Pa., pp. 164, 165 & 228.
The Dispensatory of U.S.A. 24th Ed. (1947), J. B. Lippincott Co., Phila., Pa., pp. 1054, 1055, 1459 & 1460.
The National Dispensatory (1879), pp. 650 & 651.

*Primary Examiner*—Donald B. Moyer
*Attorney, Agent, or Firm*—Joseph Zallen

[57] ABSTRACT

A medication for the relief of the discomfort associated with cold sores, lesions of the mouth commonly known as canker sores, and herpes simplex virus, which medication is a mixture of kelp and a vehicle which may be glycerin that acts as a carrier for the active ingredients of kelp.

1 Claim, No Drawings

MEDICATION FOR HERPES SIMPLEX AND CANKER SORES

BACKGROUND OF THE INVENTION

1. Field of the Invention

This invention pertains to medications for the relief of the discomfort associated with cold sores, lesions of the mouth commonly known as canker sores, and herpes simplex virus. It utilizes kelp as an active agent which pocesses the active ingredients.

2. Description of the Priot Art

Heretofore, preparations offered for the relief of the discomfort of irritations of the mucous membranes, primarily related to the mouth, contained substances such as benzocaine used as a local anesthetic; or substances such as myrrh, a bitter gum resin, used as a remedy by local application; or other preparations such as alum which has a sweetish, sourish astringent taste. These preparations including silver nitrate used to cauterize the sore and others commercially available for medicinal purposes pertaining to the cure of herpes simplex virus, cold sores on the lips and skin, and canker sores have been found by the inventor to be ineffective in giving adequate relief from the discomfort associated therewith. The period of time required for a lesion to heal itself is approximately two weeks, even with the use of standard commercially available medicines. In contrast thereto, the substance which is the subject of the present invention has been found to bring relief and to effect healing much more quickly. In one test by the inventor, relief was obtained within two minutes and a cure within twenty-four hours. Prior art medications act primarily as an antiseptic and as an anesthetic and not as a cure, while the lesions, blisters, and sores heal by themself. The medication of this invention is an effective cure.

SUMMARY OF THE INVENTION

This invention pertains to a medication for the relief of the discomfort associated with cold sores, herpes simplex virus, and lesion associated with the skin and mucous membrane linings of the body primarily, but not necessarily, occuring within the mouth commonly known as canker sores, which medication is a mixture of kelp, the active agent, and a vehicle such as glycerin which acts as a carrier for the active agent.

To prepare the medication of this invention, one mixes a quantity of kelp with a suitable quantity of a vehicle such as glycerin, according to the following considerations. Kelp is the active agent and only a small quantity is required. Whatever vehicle is used, the viscosity of the mixture may be varied by appropriate addition of the vehicle to the kelp depending on whether one desires the medication in the form of a paste, a viscous fluid, or a free-flowing liquid. The quantity of kelp mixed within substances which act as a vehicle should be great enough to ensure that the active ingredients contained within the kelp will come in contact with the affected area. The vehicle may be any substance which can carry substances such as kelp suspended thereon or contained therein. The vehicle should be safe to use in contact with the skin, lips, and various mucous membranes.

The active ingredients contained in kelp act to prevent and diminish the lesions and blisters due to the herpes simplex virus, cold sores, and canker sores. Glycerin acts as a carrier for kelp and must be used in sufficient quantity to assure the application of kelp to the affected area. Glycerine or any suitable substance besides being a carrier for the active ingredients of kelp may have a soothing effect upon the affected area. In addition to the topical application to the affected area, the mixture of kelp and glycerin may be taken internally simultaneously.

DESCRIPTION OF THE PREFERRED EMBODIMENT

In the preferred embodiment, a viscous mixture contains ten fluid ounces of glycerin and ten ounces of kelp. If a more liquid mixture of a lower viscosity is desired an additional ten fluid ounces of glycerin may be added. The mixture of kelp and glycerin provides a medication for the relief of discomfort associated with cold sores, herpes simplex virus, canker sores, and sores associated with the mucous membrane linings of the body.

Applied topically, kelp is the active agent which contains the active ingredients and it must be brought into direct contact with the affected area. The active ingredients contained within kelp act to prevent and diminish the lesions and blisters due to herpes simplex virus, contain and diminish cold sores and canker sores. The mixture of kelp and glycerin may be taken internally simultaneously with topical application of the mixture to the affected area. Glycerin acts as a carrier for the kelp which is in powdered and granular form and must be in sufficient quantity as a carrier to effect a mixture and to effect direct contact with the affected area. Both the quantity and the viscosity of the vehicle may be changed without altering the final effect of the medication as would occur by substituting mineral oil for glycerin although, in the case of a more dilute mixture, several treatments may be required. Treatment may be used as frequently as required. The vehicle which acts as a carrier may be any medium suitable for the application to the mucous membranes.

I claim:

1. The method of treatment of herpes simplex virus, cold sores, lesions and blisters affecting mucous membranes of the mough comprising topical application of kelp to the affected area.

* * * * *